(12) United States Patent
Asai et al.

(10) Patent No.: US 12,078,794 B2
(45) Date of Patent: Sep. 3, 2024

(54) ENDOSCOPE

(71) Applicant: OLYMPUS CORPORATION, Tokyo (JP)

(72) Inventors: Risako Asai, Kawagoe (JP); Mikio Inomata, Fuchu (JP)

(73) Assignee: OLYMPUS CORPORATION, Tokyo (JP)

( * ) Notice: Subject to any disclaimer, the term of this patent is extended or adjusted under 35 U.S.C. 154(b) by 565 days.

(21) Appl. No.: 17/111,695

(22) Filed: Dec. 4, 2020

(65) Prior Publication Data
US 2021/0085166 A1 Mar. 25, 2021

Related U.S. Application Data

(63) Continuation of application No. PCT/JP2019/008996, filed on Mar. 7, 2019.

(30) Foreign Application Priority Data

Jun. 5, 2018 (JP) ................................ 2018-108021

(51) Int. Cl.
*G02B 23/24* (2006.01)
*A61B 1/00* (2006.01)
(Continued)

(52) U.S. Cl.
CPC ...... *G02B 23/2423* (2013.01); *A61B 1/00096* (2013.01); *A61B 1/00163* (2013.01);
(Continued)

(58) Field of Classification Search
CPC ......... A61B 1/00096; A61B 1/05; A61B 1/04; A61B 1/00188; A61B 1/00163; A61B 1/045; A61B 1/051; A61B 1/00193; A61B 1/0008; A61B 1/0019; A61B 1/000194; A61B 1/002; G02B 23/243; G02B 23/2438; G02B 7/02
(Continued)

(56) References Cited

U.S. PATENT DOCUMENTS

2005/0267328 A1* 12/2005 Blumzvig .......... G02B 13/0065
348/E5.029
2008/0167529 A1* 7/2008 Otawara .................. A61B 1/07
600/168
(Continued)

FOREIGN PATENT DOCUMENTS

EP 2605053 A1 6/2013
EP 2881774 A1 6/2015
(Continued)

OTHER PUBLICATIONS

International Search Report dated May 28, 2019 issued in PCT/JP2019/008996.

*Primary Examiner* — Ryan N Henderson
*Assistant Examiner* — Pamela F Wu
(74) *Attorney, Agent, or Firm* — Scully, Scott, Murphy & Presser, P.C.

(57) ABSTRACT

An endoscope includes a first frame, a second frame, a first clearance, an enlarged diameter section, a distal end constituent member, and a second clearance, and a set height of the enlarged diameter section is set to be greater than a magnitude of the first clearance to which the second clearance is added.

18 Claims, 8 Drawing Sheets

(51) Int. Cl.
*A61B 1/05* (2006.01)
*G02B 7/02* (2021.01)

(52) U.S. Cl.
CPC .................. *A61B 1/05* (2013.01); *G02B 7/02* (2013.01); *G02B 23/243* (2013.01)

(58) Field of Classification Search
USPC ......... 600/101, 163, 167–168, 172–175, 160
See application file for complete search history.

(56) References Cited

U.S. PATENT DOCUMENTS

| | | | |
|---|---|---|---|
| 2009/0076332 A1* | 3/2009 | Iwasaki | A61B 1/0019 600/168 |
| 2009/0093681 A1* | 4/2009 | Ichimura | A61B 1/0623 600/178 |
| 2013/0027534 A1 | 1/2013 | Kibayashi | |
| 2015/0156381 A1 | 6/2015 | Oba | |
| 2016/0302647 A1 | 10/2016 | Orihara et al. | |
| 2016/0377855 A1* | 12/2016 | Takata | G02B 23/2438 359/696 |
| 2017/0139198 A1* | 5/2017 | Kibayashi | A61B 1/00045 |
| 2017/0296044 A1* | 10/2017 | Wataya | H04N 23/55 |

FOREIGN PATENT DOCUMENTS

| | | |
|---|---|---|
| JP | H10-160993 A | 6/1998 |
| JP | 2003-230532 A | 8/2003 |
| JP | 2009-148369 A | 7/2009 |
| JP | UP 5315482 B1 | 10/2013 |
| JP | 2015-047358 A | 3/2015 |
| WO | WO 2012/137739 A1 | 10/2012 |
| WO | WO 2014/020987 A1 | 2/2014 |
| WO | WO 2015/174444 A1 | 11/2015 |
| WO | WO-2017022279 A1 * 2/2017 ......... A61B 1/00096 |

* cited by examiner

ENDOSCOPE

CROSS REFERENCE TO RELATED APPLICATION

This application is a continuation application of PCT/JP2019/008996 filed on Mar. 7, 2019 and claims benefit of Japanese Application No. 2018-108021 filed in Japan on Jun. 5, 2018, the entire contents of which are incorporated herein by this reference.

BACKGROUND OF THE INVENTION

1. Field of the Invention

The present invention relates to an endoscope including a first frame configured to hold a first optical system and a second frame configured to hold the second optical system and fitted to the proximal end side of the first frame.

2. Description of the Related Art

In recent years, endoscopes have been widely used in medical and industrial fields. An endoscope can observe an interior of a subject by using an image pickup unit provided in an elongated insertion section by inserting the insertion section into the subject.

The image pickup unit includes an objective lens unit. In the objective lens unit, one or more optical systems are held by a lens frame.

The image pickup unit further includes an image pickup device, such as a CCD and CMOS device, that is held by a device frame on the proximal end side with respect to the objective lens unit in the optical axis direction of the optical system and configured to pick up an image of the interior of the subject via the optical system.

The image pickup unit further includes a substrate which is electrically connected to the image pickup device and on which electronic parts are mounted, a cable that is electrically connected to the substrate and configured to transmit and receive an electric signal to and from the substrate, and other components.

As the objective lens unit, there is a known configuration including a first frame configured to hold a first optical system including an objective lens exposed via a distal end surface at a distal end section of the insertion section and a second frame that is fitted to the proximal end side of the first frame in the optical axis direction and configured to hold a second optical system.

There is also a known configuration in which the second frame further includes a zoom lens frame configured to hold a zoom lens for magnification change and the device frame described above and other components are fitted to the second frame.

In the aforementioned image pickup unit including the first frame and the second frame, it is important to align the first optical system and the second optical system with each other in the radial direction in order to satisfy specified optical characteristics.

Japanese Patent Application Laid-Open Publication No. 2003-230532 discloses the configuration of an endoscope including an image pickup unit in which the distal-end inner circumference of the second frame is closely fitted and fixed to the proximal-end outer circumference of the first frame in the optical axis direction.

In recent years, there has been a known endoscope capable of outputting a combined image generated by combining images taken in near view with those taken in far view as a single stereoscopic image.

Such an endoscope has a configuration in which a prism is provided on the rearward side of the second optical system in the optical axis direction, separates images of a subject acquired by the first optical system and the second optical system into at least two optical images having different optical path lengths, and causes the optical images to be formed on the image pickup device.

In such an endoscope, it is known that the first optical system and the second optical system need to be aligned with each other in the radial direction more precisely than in the configuration of a typical image pickup unit.

There is also a known configuration in which a radial-direction clearance is provided in the portion where the first frame and the second frame are fitted to each other to allow the first optical system and the second optical system to be precisely aligned with each other in the radial direction with the clearance.

To prevent moisture from traveling toward the image pickup device via the clearance, there is also known configuration in which an enlarged diameter section is provided around the outer circumference of the first frame and the enlarged diameter section abuts, for example, on a distal end constituent member that forms a distal end section of the endoscope on the frontward side of the fitting portion described above in the optical axis direction.

Examples of the cause of the entry of moisture include specific use of an endoscope, such as autoclave sterilization after use of the endoscope and the fact that the interior of a body cavity is under a high humidity environment when the subject is the body cavity.

SUMMARY OF THE INVENTION

An endoscope according to an aspect of the present invention includes a first frame configured to hold a first optical system, a second frame configured to hold a second optical system located on a rearward side of the first optical system in an optical axis direction of the first optical system, the second frame being fitted to a proximal end side of the first frame in the optical axis direction, a first clearance provided in a radial direction of the first frame and the second frame in a fit portion where the first frame and the second frame are fitted to each other, an enlarged diameter section provided in the first frame and enlarged radially from the first frame by a height set outward in the radial direction, an endoscope constituent member including a portion on which the enlarged diameter section abuts on a distal end side with respect to the enlarged diameter section in the optical axis direction, and a second clearance provided in the radial direction between an outer circumference of the first frame and the portion of the endoscope constituent member on which the enlarged diameter section abuts, and the set height of the enlarged diameter section is set to be greater than a magnitude of the first clearance to which the second clearance is added.

DETAILED DESCRIPTION OF THE PREFERRED EMBODIMENTS

Figure 1:
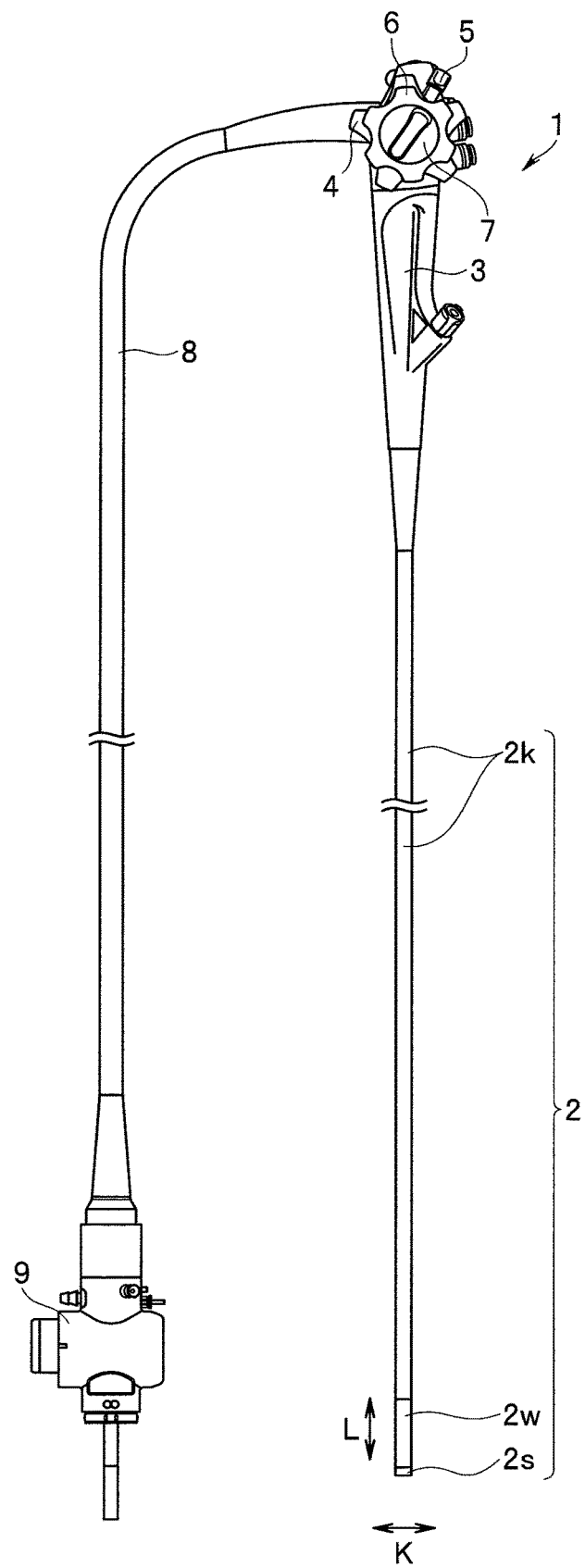
FIG. 1 shows an exterior appearance of an endoscope according to a present embodiment.

An embodiment of the present invention will be described below with reference to the drawings. In the respective drawings used in the description below, each component is drawn at different scales to be large enough to be recognizable in the drawings. In other words, the present invention is not limited only to the number of components, the shapes of the components, the size ratio among the components, and the relative positional relationship among the respective components shown in the drawings.

FIG. 1 shows an exterior appearance of an endoscope according to the present embodiment.

An endoscope 1 primarily includes an insertion section 2, which is inserted into a subject, an operation section 3, which is provided contiguously to a proximal end side of the insertion section 2 in an optical axis direction L, which will be described later, a universal code 8, which extends from the operation section 3, and a connector 9, which is provided at an extended end of the universal code 8, as shown in FIG. 1. The endoscope 1 is electrically connected to an external apparatus, such as a controller and an illuminator, via the connector 9.

The operation section 3 is provided with an upward/downward bending operation knob 4 configured to allow a bending section 2w, which will be described later, of the insertion section 2 to bend in an upward/downward direction and a rightward/leftward bending operation knob 6 configured to allow the bending section 2w to bend in a rightward/leftward direction.

The operation section 3 is further provided with a fixing lever 5 configured to fix a pivotal position of the upward/downward bending operation knob 4 and a fixing knob 7 configured to fix a pivotal position of the rightward/leftward bending operation knob 6.

The insertion section 2 is an elongated section and includes a distal end section 2s, the bending section 2w, and a flexible tube section 2k sequentially arranged from the distal end side in the optical axis direction L.

The bending section 2w is bent, for example, in four directions, the upward/downward directions and the rightward/leftward directions, by operation of rotating the upward/downward bending operation knob 4 and the rightward/leftward bending operation knob 6.

The bending section 2w therefore changes an observation direction of an image pickup unit 100 (see FIG. 2), which will be described later and is provided in the distal end section 2s, and improves insertability of the distal end section 2s in the subject. Further, the flexible tube section 2k is provided contiguously to the proximal end side of the bending section 2w in the optical axis direction L.

The image pickup unit 100 is provided in the distal end section 2s, which is provided contiguously to the distal end side of the bending section 2w in the optical axis direction L and forms the distal end side of the insertion section 2 in the optical axis direction L.

Figure 2:
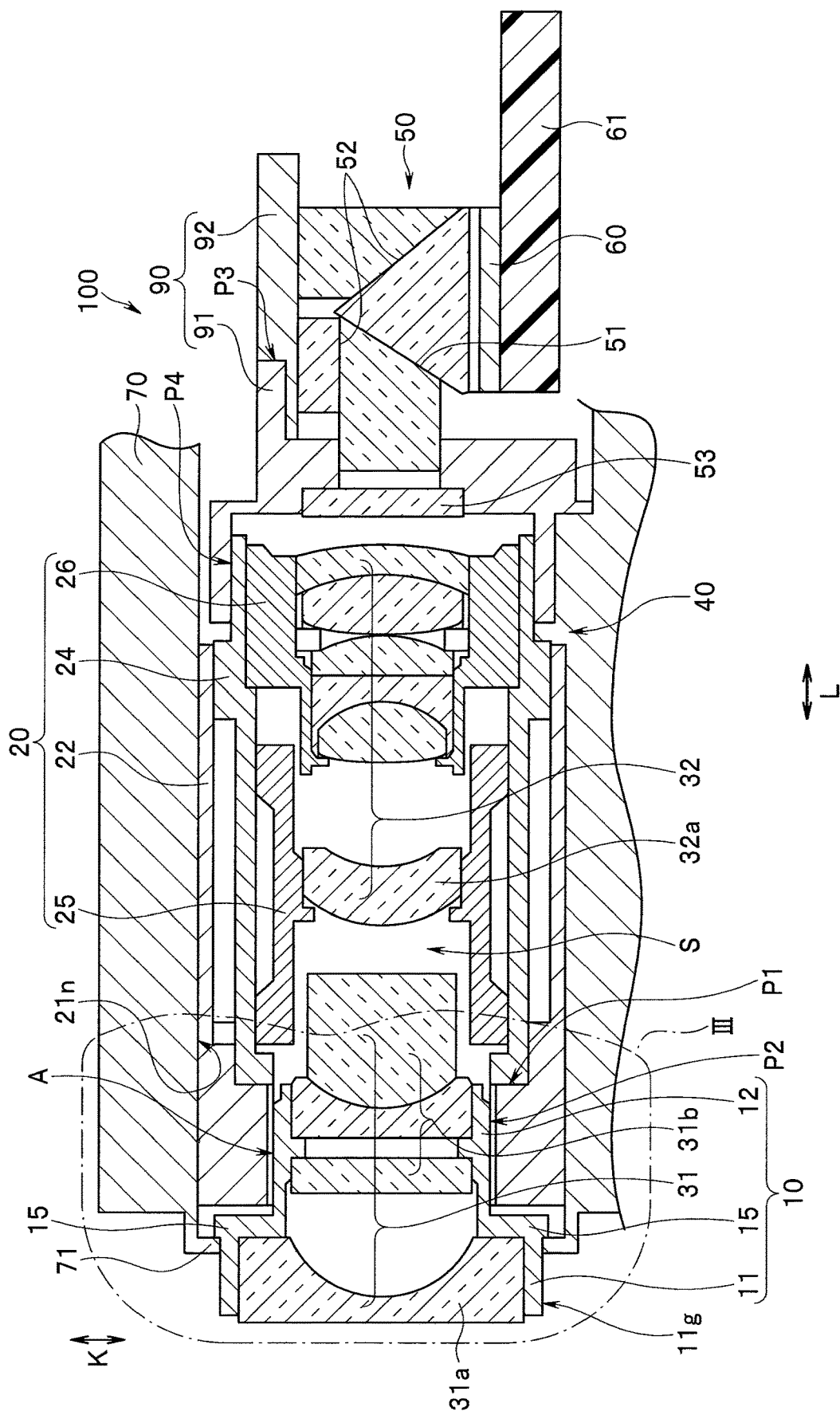
FIG. 2 schematically shows a cross section of an image pickup unit and a distal end constituent member provided in a distal end section of an insertion section of the endoscope shown in FIG. 1.
Figure 3:
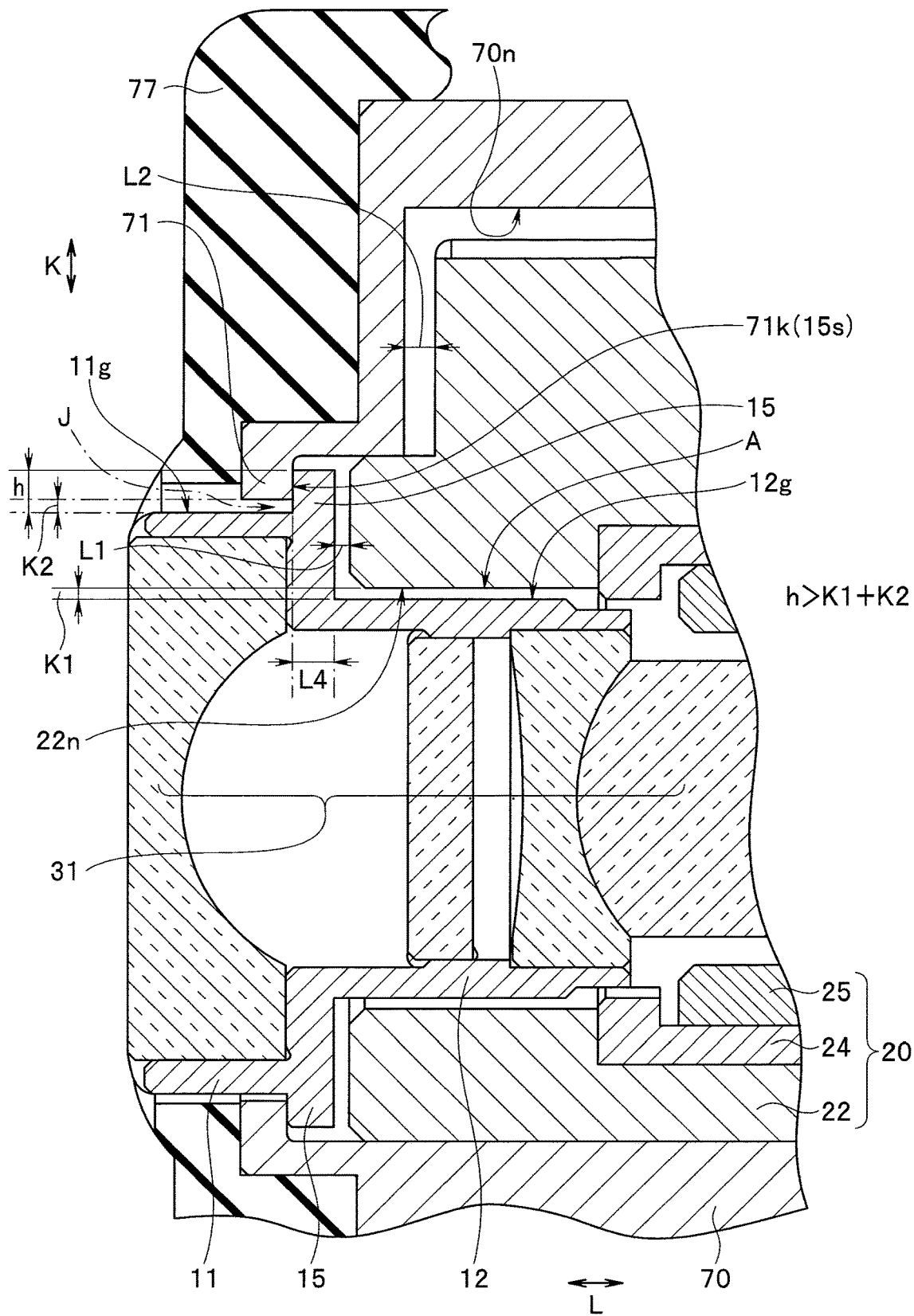
FIG. 3 is an enlarged partial cross-sectional view showing a portion surrounded by a line III in FIG. 2 in the image pickup unit shown in FIG. 2 along with a distal end cover.

A configuration of the image pickup unit 100 will next be described with reference to FIGS. 2 and 3. FIG. 2 schematically shows a cross section of the image pickup unit and a distal end constituent member provided in the distal end section of the insertion section of the endoscope shown in FIG. 1, and FIG. 3 is an enlarged partial cross-sectional view showing a portion surrounded by a line III in FIG. 2 in the image pickup unit shown in FIG. 2 along with a distal end cover.

The image pickup unit 100 primarily includes an objective lens unit 40, a prism 50, and an image pickup device 60, which is an image pickup member, as shown in FIG. 2.

The objective lens unit 40 forms the distal end section 2s and is provided in a space S of a distal end constituent member 70, which is an endoscope constituent member.

A distal end cover 77 covers an outer circumference of the distal end constituent member 70 and a distal end of the distal end constituent member 70 in the optical axis direction L in such a way that part of the distal end cover 77 circumferentially faces in a radial direction K an outer circumference 11g of a distal end side portion 11 of a first frame 10, which will be described later.

The objective lens unit 40 includes the first frame 10 configured to hold a first optical system 31 including an objective lens 31a exposed via the distal end surface of the distal end section 2s, and a second frame 20 configured to hold a second optical system 32.

The first frame 10 primarily includes the distal end side portion 11 configured to hold the objective lens 31a in the first optical system 31, a proximal end side portion 12 configured to hold a rear side lens group 31b in the first optical system 31, and an enlarged diameter section 15.

The proximal end side portion 12 is located on the proximal end side with respect to the distal end side portion 11 in the optical axis direction L1 of the first optical system 31 and located inside the first frame 10 with respect to the distal end side portion 11 in the radial direction K. In other words, the proximal end side portion 12 is formed to be smaller in diameter than the distal end side portion 11.

The enlarged diameter section 15 is located between the distal end side portion 11 and the proximal end side portion 12 in the optical axis direction L and has an outward flange shape that circumferentially extends by a set height h outward in the radial direction K from the outer circumference 11g of the distal end side portion 11, as shown in FIG. 3. The enlarged diameter section 15 has a length L4 in the optical axis direction L.

The enlarged diameter section 15 may be integrally formed with the first frame 10 or may be formed separately from the first frame 10 and fixed to the first frame 10.

A reduced diameter section 71 protrudes inward in the radial direction K from the distal end side with respect to the enlarged diameter section 15 in the optical axis direction L to face the outer circumference 11g. The enlarged diameter section 15 circumferentially abuts on the reduced diameter section 71 in the optical axis direction L at an inner circumferential surface 70n of the distal end constituent member 70. In other words, the reduced diameter section 71 forms a portion on which the enlarged diameter section 15 in the present embodiment abuts.

A flat surface 15s, which is in close contact with a surface 71k of the reduced diameter section 71 that is a surface on the proximal end side in the optical axis direction L, is provided on the distal end side of the enlarged diameter section 15 in the optical axis direction L.

The position where the enlarged diameter section 15 abuts on the reduced diameter section 71 in the optical axis direction L may be any position on the frontward side of a fit portion A, which will be described later, in the optical axis direction L.

Since the flat surface 15s of the enlarged diameter section 15 abuts on the surface 71k of the reduced diameter section 71, the position of the first frame 10 in the optical axis direction L with respect to the distal end constituent member 70 is determined.

The enlarged diameter section 15 abuts on the reduced diameter section 71 to prevent moisture J, which enters a later-described second clearance K2 from the front side in the optical axis direction L, from entering a later-described first clearance K1.

The second frame 20 is fitted to a proximal end side outer circumference of the first frame 10 in the optical axis direction L, that is, an outer circumference of the proximal end side portion 12 and holds the second optical system 32, which is located on the rearward side with respect to the first optical system 31 in the optical axis direction L.

The second frame 20 may be fitted to a proximal end side inner circumference of the first frame 10 in the optical axis direction L.

The second frame 20 primarily includes a first linkage frame 22, a second linkage frame 24, a moving lens frame 25, and a lens holding frame 26.

The first linkage frame 22 forms a portion of the second frame 20 that is the portion fitted to the outer circumference of the proximal end side portion 12 of the first frame 10 in the fit portion A.

The second frame 20 may be integrally formed of the first linkage frame 22, the second linkage frame 24, the moving lens frame 25, and the lens holding frame 26 integrated with one another.

A distal end side inner circumference of a device frame 90 is fitted and fixed to a proximal end side outer circumference of the second linkage frame 24.

The device frame 90 primarily includes a first device frame 91 configured to hold a distal end side of an optical system 53 and the prism 50 in the optical axis direction L, and a second device frame 92 configured to hold the prism 50 and the image pickup device 60 electrically connected to a substrate 61.

The prism 50 is located on the rearward side of the second optical system 32 in the optical axis direction L, separates images of a subject acquired by the first optical system 31 and the second optical system 32 into at least two optical images having different optical path lengths, and causes the optical images to be formed on the image pickup device 60.

More specifically, the prism 50 separates, by using a deflection plate 51 and a reflection plate 52, light made incident via the first optical system 31 and the second optical system 32 into, for example, two optical images, causes refractive indices of the optical images to be different from each other, and changes the optical path lengths that form an image on the image pickup device 60.

The optical images having passed through a lens 32a, which form the second optical system 32 held by the moving lens frame 25 and is provided in a predetermined position, pass through the prism 50, and the image pickup device 60 picks up, for example, two optical images, a first optical image brought into focus in the vicinity of a far point observation area and a second optical image brought into focus in the vicinity of a near point observation area.

An image processing section provided in a processor that is not shown then combines two image portions of the first and second optical images that are picked-up portions brought into focus with each other, and the processor causes a display unit that is not shown to display one image having a wide depth of field.

The first clearance K1 is formed, in the radial direction K, in the fit portion A between an outer circumference 12g of the proximal end side portion 12 of the first frame 10 and an inner circumference 22n of the first linkage frame 22, as shown in FIG. 3.

The first clearance K1 is used to precisely align the second optical system 32 with respect to the first optical system 31 in the radial direction K and is a movement area where either the first frame 10 or the first linkage frame 22 is moved in the radial direction K. The first clearance K1 is an area filled, for example, with an adhesive that is not shown after the alignment.

A clearance L1 is formed in the optical axis direction L between the enlarged diameter section 15 and a distal end of the first linkage frame 22.

The clearance L1 is used to precisely align the first linkage frame 22 with respect to the first frame 10 in the optical axis direction L and is a movement area where either the first frame 10 or the first linkage frame 22 is moved in the optical axis direction L. The clearance L1 is an area filled, for example, with an adhesive that is not shown after the alignment.

Figure 4:
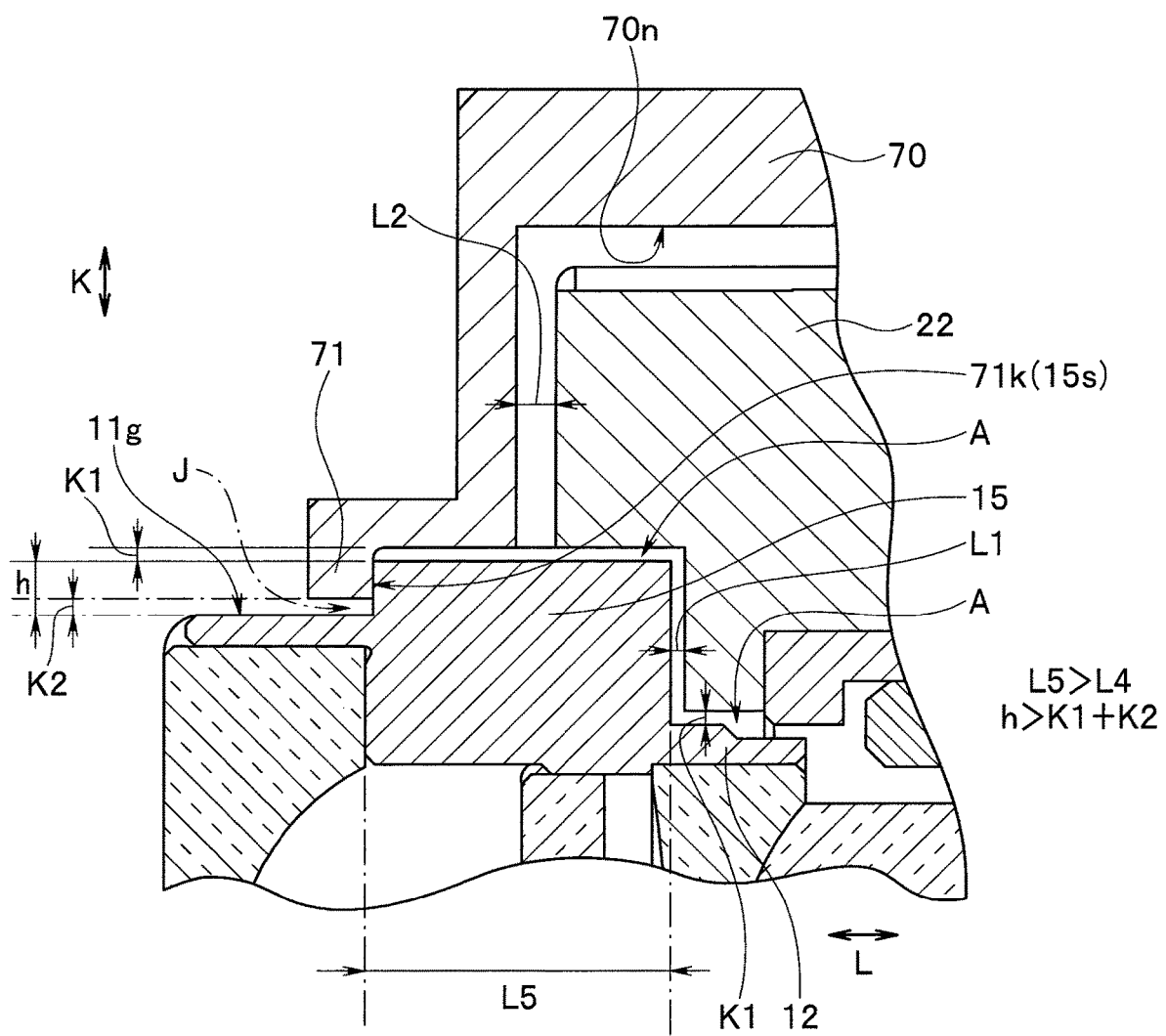
FIG. 4 is a partial cross-sectional view of an image pickup unit according to a modification of a shape of an enlarged diameter section with which a first frame is provided shown in FIG. 3.

Further, a clearance L2 is formed in the optical axis direction L between the distal end constituent member 70 and the distal end of the first linkage frame 22, as shown in FIG. 4.

The clearance L2 is provided, when the second optical system 32 and the first optical system 31 are precisely aligned with each other in the optical direction, to prevent the surface 71k of the reduced diameter section 71 and the distal end surface of first linkage frame 22 from interfering with each other even when the distance from the surface 71k to the distal end surface changes, and the clearance L2 is a movement area where either the distal end constituent member 70 or the first linkage frame 22 is moved in the optical axis direction L. The clearance L2 is an area filled, for example, with an adhesive that is not shown after the alignment.

In other words, the clearances L1 and L2 are necessary for the precise alignment of the second optical system 32 with respect to the first optical system 31 in the optical axis direction L.

The second clearance K2 is formed in the radial direction K between the outer circumference 11g of the distal end side portion 11 of the first frame 10 and the reduced diameter section 71.

The second clearance K2 is necessary, when the first clearance K1 is used to precisely align the second optical system 32 with respect to the first optical system 31 in the radial direction K, to move either the first frame 10 or the first linkage frame 22 in the first clearance K1 in the radial direction K.

Further, when the first clearance K1 is used to precisely align the second optical system 32 with respect to the first optical system 31 in the radial direction K, the conditions below need to be satisfied to maintain the state of the enlarged diameter section 15 that abuts on the reduced diameter section 71.

More specifically, the set height h of the enlarged diameter section 15 needs to be set to be greater than a magnitude of the first clearance K1 to which the second clearance K2 is added (h>K1+K2).

Conversely, when the set height h is set to be greater than the magnitude of the first clearance K1 to which the second clearance K2 is added, the enlarged diameter section 15 continues to abut on the reduced diameter section 71 even when the first clearance K1 is used to precisely align the second optical system 32 with respect to the first optical system 31 in the radial direction K.

In other words, the moisture J will not enter the first clearance K1 via the second clearance K2.

To assemble the configured image pickup unit 100 and attach the image pickup unit 100 to the distal end constituent member, the second linkage frame 24 to which the lens holding frame 26 has been fixed is first caused to abut on the first linkage frame 22 in a position P1 in the optical axis direction L and is bonded and fixed to first linkage frame 22, as shown in FIG. 2.

The second linkage frame 24 to which the lens holding frame 26 has been fixed is thus positioned with the first linkage frame 22 in the optical axis direction L and the radial direction K.

The first clearance K1 and the clearances L1 and L2 are then used to adjust a focal point of the second optical system 32 with respect to the first optical system 31, and a position of the first linkage frame 22 with respect to the first frame 10 in the radial direction K and the optical axis direction L is adjusted. The fit portion A is then fixed and bonded in a position P2. In other words, the first clearance K1 and the clearances L1 and L2 are filled with an adhesive.

The second device frame 92 is then caused to abut on the first device frame 91 in the optical axis direction L so that the position of the second device frame 92 in the radial direction K and the optical axis direction L is adjusted, followed by bonding and fixation of the second device frame 92, and the position of the first device frame 91 is then adjusted with respect to the second linkage frame 24 in the radial direction K and the optical axis direction L, followed by bonding and fixation of the first device frame 91.

Finally, the enlarged diameter section 15 is caused to abut on the reduced diameter section 71 in the optical axis direction L, whereby the first frame 10 and the second frame 20 are positioned in the optical axis direction L with respect to the distal end constituent member 70.

Other components and methods of assembling the image pickup unit 100 are well known and will therefore not be described.

As described above, in the present embodiment, the first clearance K1 is formed in the radial direction K in the fit portion A between the outer circumference 12g of the proximal end side portion 12 of the first frame 10 and the inner circumference 22n of the first linkage frame 22.

Further, the second clearance K2 is formed in the radial direction K between the outer circumference 11g of the distal end side portion 11 of the first frame 10 and the reduced diameter section 71.

The set height h of the enlarged diameter section 15 is set to be greater than the magnitude of the first clearance K1 to which the second clearance K2 is added (h>K1+K2).

The first clearance K1 thus allows precise adjustment of the position of the second optical system 32 in the radial direction K with respect to the first optical system 31 to a position where optical performance of the first optical system 31 and the second optical system 32 is maximized.

In particular, when a plurality of optical systems need to be precisely positioned with respect to each other, as in the present embodiment, in which light incident via the first optical system 31 and the second optical system 32 is separated by the prism 50 into a plurality of optical images and the plurality of optical images having different focal points are correctly formed in a predetermined position of the image pickup device 60, an adjustment margin for precise adjustment that allows best optical performance can be reliably provided.

Further, the configuration in which the set height h is set to be greater than the magnitude of the first clearance K1 to which the second clearance K2 is added allows the state in which the enlarged diameter section 15 abuts on the reduced diameter section 71 along the entire circumference to be maintained even when the first clearance is used to move either the first frame 10 or the second frame 20 in the radial direction K to adjust the position of the second frame 20 with respect to the first frame 10.

Therefore, since the enlarged diameter section 15 that abuts on the reduced diameter section 71 reliably prevents moisture J from entering a first clearance K1 via the second clearance K2, dimness and trouble of a field of view can be avoided.

The endoscope 1 provided as described above has the configuration in which the first optical system 31 and the second optical system 32 can be precisely aligned with each other in the radial direction K and the enlarged diameter section can reliably prevent entry of moisture.

A modification of the embodiment will be shown with reference to FIG. 4. FIG. 4 is a partial cross-sectional view of an image pickup unit according to a modification of the shape of the enlarged diameter section with which the first frame is provided shown in FIG. 3.

As described above, in the present embodiment, the enlarged diameter section 15 has an outward flange shape having the length L4 in the optical axis direction L.

The configuration of the enlarged diameter section 15 is not limited to the above, and the enlarged diameter section 15 may have a cylindrical shape having a length L5 greater than L4 in the optical axis direction L (L5>L4), as shown in FIG. 4, and such an enlarged diameter section can provide the same effects as the effects provided in the present embodiment described above.

Figure 5:
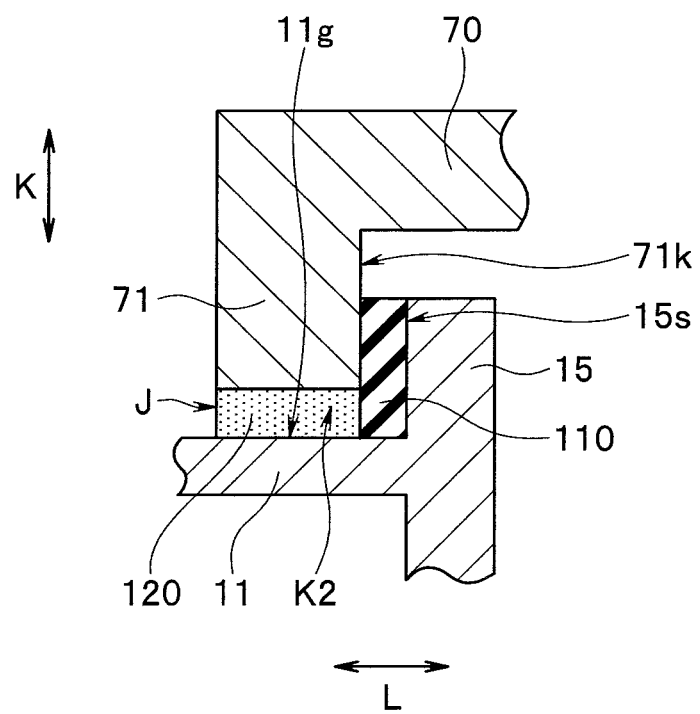
FIG. 5 is a partial cross-sectional view of an image pickup unit according to a modification in which a close contact member is provided between a reduced diameter section and the enlarged diameter section shown in FIG. 3.

FIG. 5 shows another modification of the embodiment below. FIG. 5 is a partial cross-sectional view of an image pickup unit according to a modification in which a close contact member is provided between the reduced diameter section and the enlarged diameter section shown in FIG. 3.

To prevent the entrance of the moisture J into the first clearance K1 via the second clearance K2, a close contact member 110, which improves the close contact of the flat surface 15s with the surface 71k, such as a gasket, may be provided between the reduced diameter section 71 and the enlarged diameter section 15 in the optical axis direction L, as shown in FIG. 5.

Further, an adhesive 120 may be injected into the second clearance K2 from the distal end side in the optical axis direction L.

Other effects are the same as the other effects in the present embodiment described above.

In the present embodiment described above, the enlarged diameter section 15 abuts on the reduced diameter section 71 of the distal end constituent member 70.

The configuration of the enlarged diameter section 15 is not limited to the above, and the member on which the enlarged diameter section 15 abuts may, of course, be another member on the distal end side with respect to the fit portion A in the optical axis direction L, for example, the distal end cover 77 or another member provided in the distal end section 2s.

Further, in the present embodiment described above, a mechanism that requires precise positioning, such as the image pickup unit 100, is provided in the distal end section 2s, but is not limited to the mechanism. The same effects as the effects provided in the present embodiment described above can be provided also when a variety of optical parts or any other mechanism having clearances, a reduced diameter section, an enlarged diameter section, and the height of the enlarged diameter section related to one another in accordance with the conditions described in the present embodiment is provided either in another portion of the insertion section 2 or in the operation section 3.

In the present embodiment described above, the endoscope 1 has been described with reference to an endoscope as an example which is capable of outputting a combined image generated by combining images taken in near view with those taken in far view by the prism 50 as a single stereoscopic image.

The configuration of the endoscope applicable with the present embodiment is not limited to the above, and the present embodiment described above is applicable to another endoscope in which the second optical system 32 needs to be precisely positioned with respect to the first optical system 31 in the radial direction K.

The content of the technology of the present invention is not limited to the configuration in which the image pickup unit 100 primarily includes the objective lens unit 40, the prism 50, and the single image pickup device 60.

Figure 6:
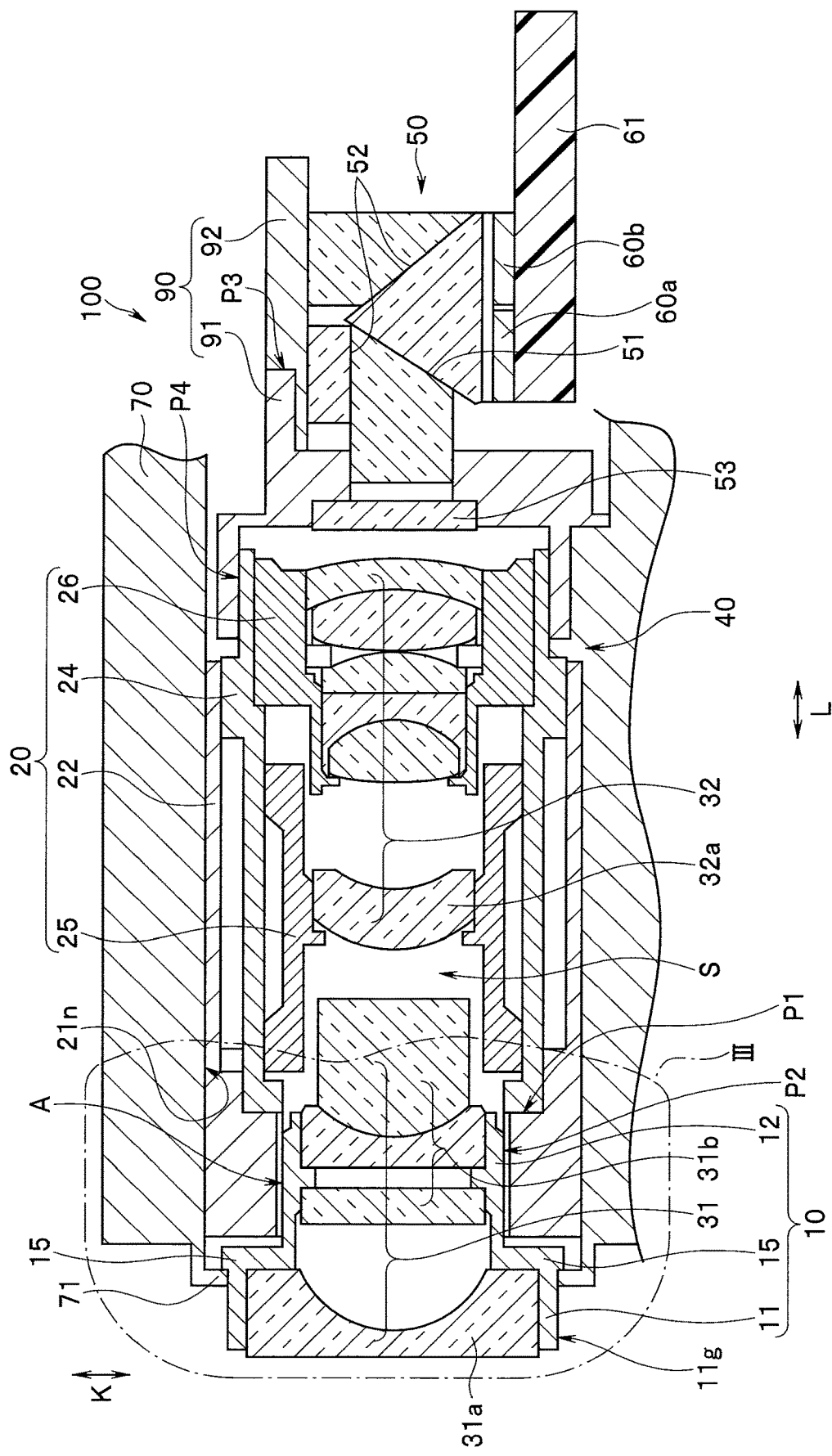
FIG. 6 shows a modification in which the image pickup unit shown in FIG. 2 includes a first image pickup device and a second image pickup device.

FIG. 6 shows a modification in which the image pickup unit shown in FIG. 2 includes a first image pickup device and a second image pickup device.

The prism 50 may separate images of a subject acquired by the first optical system 31 and the second optical system 32 into at least two optical images having different optical path lengths and cause the optical images to be formed respectively on a first image pickup device 60a and a second image pickup device 60b.

The first image pickup device 60a and the second image pickup device 60b are juxtaposed with each other in the second device frame 92.

The configuration may be applied in which the prism 50 separates, by using the reflection plate 52 and other components, light made incident via the first optical system 31 and the second optical system 32 into, for example, a first optical image and a second optical image as two optical images, causes refractive indices of lights to be different from each other in the optical path, and causes the first optical image to be formed on the first image pickup device 60a and the second optical image to be formed on the second image pickup device 60b.

Figure 7:
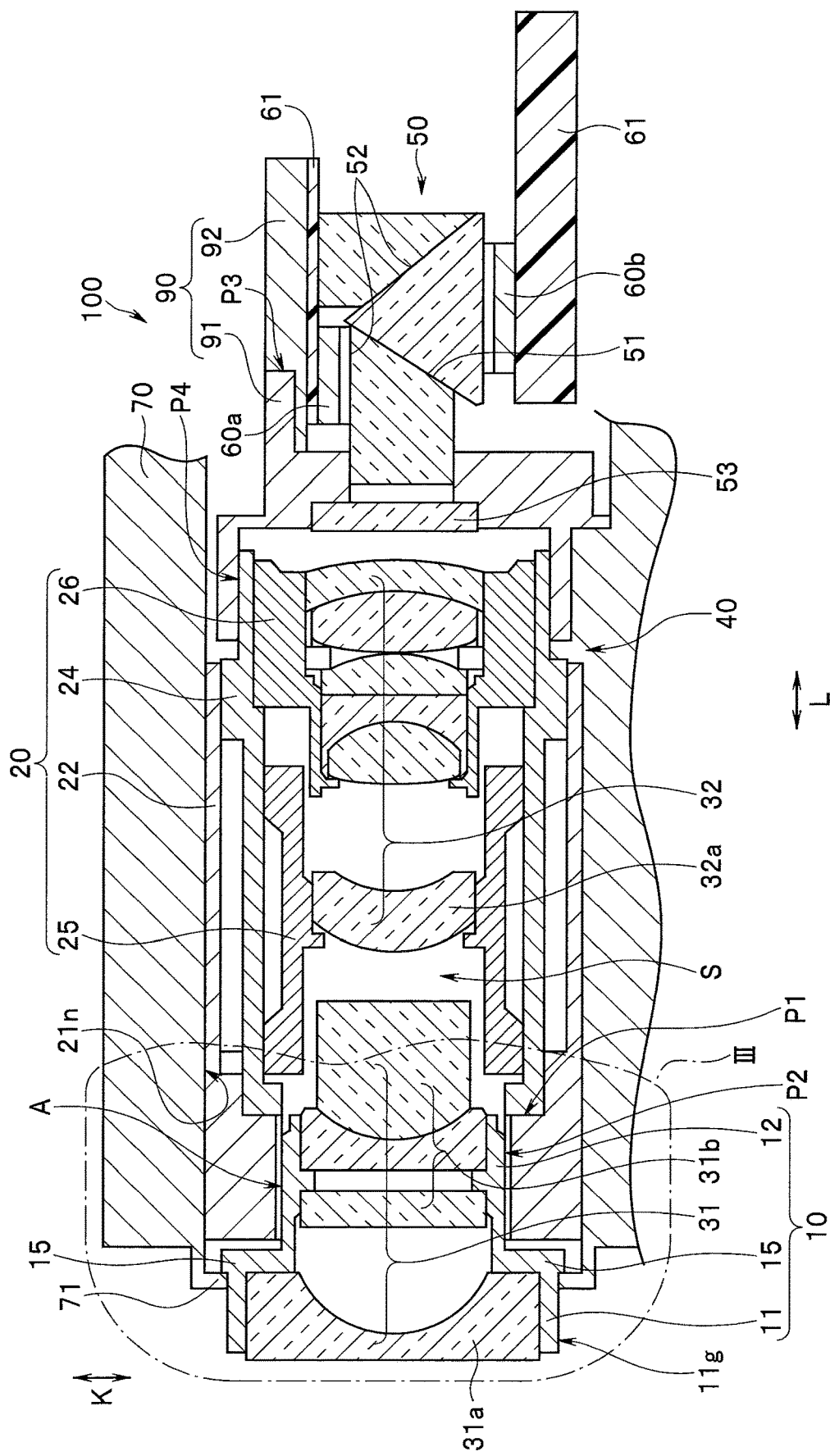
FIG. 7 shows another modification in which the image pickup unit shown in FIG. 2 includes the first image pickup device and the second image pickup device.

FIG. 7 shows another modification in which the image pickup unit shown in FIG. 2 includes the first image pickup device and the second image pickup device.

As shown in FIG. 7, the first image pickup device 60a and the second image pickup device 60b may not be juxtaposed with each other, unlike in FIG. 6.

In other words, the first optical image and the second optical image emitted from different portions of the prism 50 may be formed on the first image pickup device 60a and the second image pickup device 60b, respectively.

Figure 8:
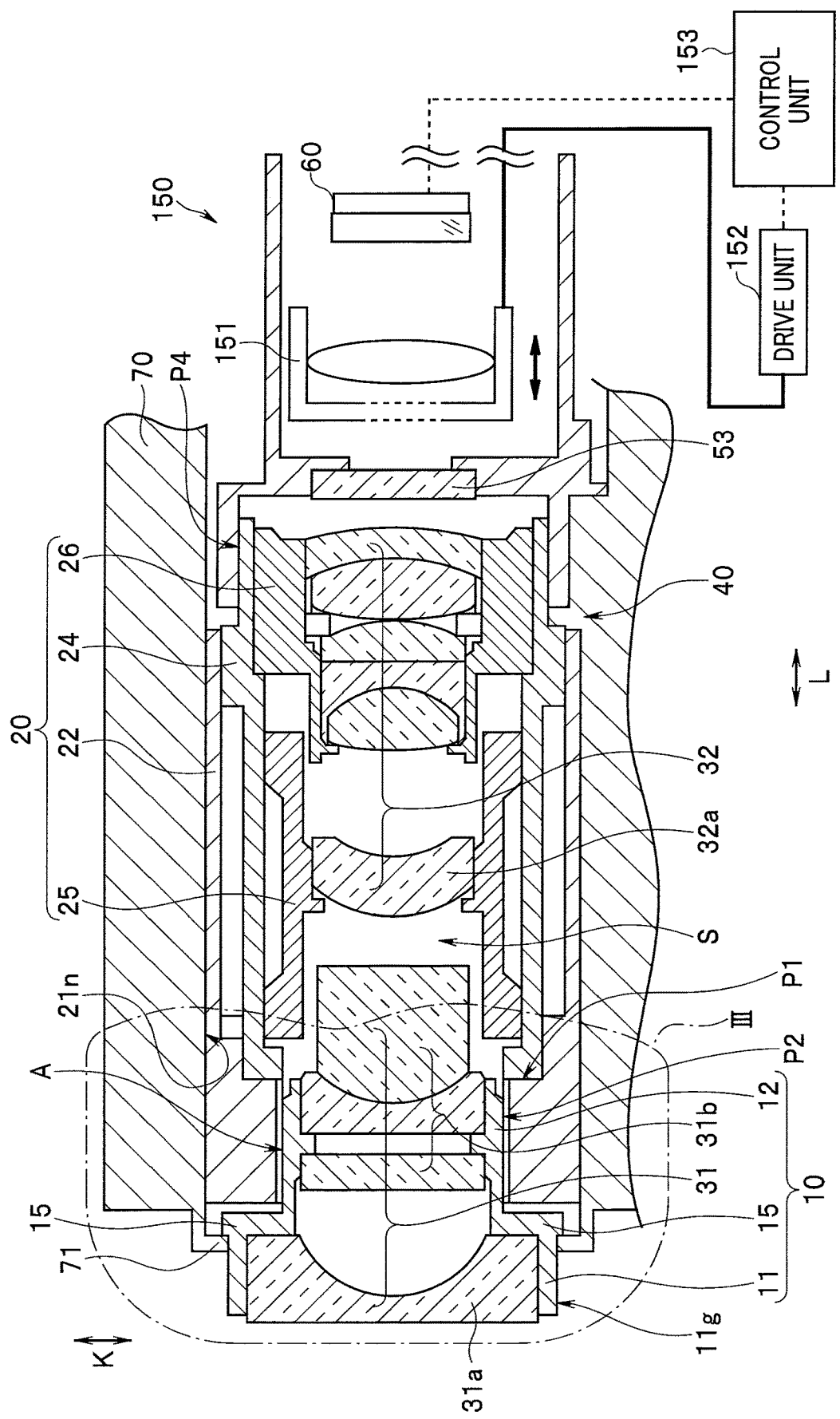
FIG. 8 shows a modification in which the image pickup unit shown in FIG. 2 includes no prism but includes a moving lens unit.

Further, FIG. 8 shows a modification in which the image pickup unit shown in FIG. 2 includes no prism but includes a moving lens unit.

The image pickup unit 100 in the present embodiment described above and in FIGS. 6 and 7 has been described with reference to the case where the prism 50 simultaneously focuses optical images on one or two image pickup devices, which acquire two optical images that are formed in different positions, two image portions of the first and second optical images that are picked-up portions brought into focus are combined with each other, and a processor causes a display unit that is not shown to display one image having a wide depth of field.

In FIG. 8, the two optical images are formed on the image pickup device at different points of time, whereby two optical images brought into focus in different positions are acquired and combined with each other into a combined image.

A moving lens unit 150 includes a moving lens 151, and images of a subject that are acquired by the first optical system 31 and the second optical system 32 pass through the moving lens 151 and are formed as optical images on the image pickup device 60.

The moving lens unit 150 includes a drive unit 152 including an actuator, such as a motor, and the drive unit 152 is provided to move the moving lens 151, for example, in a frontward/rearward direction with respect to the optical axis direction L.

The drive unit 152 and the image pickup device 60 are connected to a control unit 153 provided, for example, in an external process and driven and controlled by the control unit 153.

The control unit 153 drives the drive unit 152 to cause the moving lens unit 150 to make, for example, reciprocal motion so that the moving lens 151 reaches the different focus positions with respect to the image pickup device 60.

The moving lens 151 is set to be brought into focus in a first focus position and a second focus position different from the first focus position with respect to the image pickup device 60.

When the moving lens 151 reaches the first focus position with respect to the image pickup device 60, the control unit 153 causes the image pickup device 60 to acquire a first image.

When the moving lens 151 reaches the second focus position with respect to the image pickup device 60, the control unit 153 causes the image pickup device 60 to acquire a second image.

A video processor that is not shown but is connected to the endoscope 1 combines the acquired first image and second image with each other and outputs a resultant extended-depth-of-focus image.

Also in the aforementioned configurations described with reference to FIGS. 6 to 8, when a plurality of optical systems need to be precisely positioned with respect to each other, in which light incident via the first optical system 31 and the second optical system 32 is separated into a plurality of optical images and the plurality of optical images having different focal points are correctly formed in a predetermined position of one or more image pickup devices, an adjustment margin for precise adjustment that allows best optical performance can be reliably provided as in the present embodiment described above, based on the basic configuration of the present invention.

The present invention is not limited to the embodiment described above and can be changed as appropriate to the extent that the changes do not contradict either the gist or the idea of an invention readable from the claims and the entire specification, and an insertion tool and an endoscope resulting from the changes are encompassed within the technical range of the present invention.

What is claimed is:

1. An endoscope comprising:
    a first frame configured to hold a first optical system, the first frame comprises:
        a distal end portion;
        an enlarged portion projecting radially outward from the distal end portion by a height; and
        a proximal end portion;
    a second frame configured to hold a second optical system, the second frame fitted to the proximal end portion; and
    an endoscope constituent body including a portion that contacts a distal side of the enlarged portion;
    wherein the proximal end portion and the second frame are configured to define a first radial clearance in a radial direction between an outer circumferential surface of the proximal end portion and an inner circumferential surface of the second frame;
    the distal end portion and the endoscope constituent body are configured to define a second radial clearance in the radial direction between an outer circumferential surface of the distal end portion and an inner circumferential surface of the portion of the endoscope constituent body;
    the first frame and the second frame are configured to define a first longitudinal clearance in a longitudinal direction between a distal face of the second frame and a proximal face of the enlarged portion of the first frame, the distal face directly opposing the proximal face; and
    the height of the enlarged portion is greater than a magnitude of a sum of the first radial clearance and the second radial clearance.

2. The endoscope according to claim 1, wherein the first frame and the second frame are provided in an internal space defined by the endoscope constituent body.

3. The endoscope according to claim 2, wherein the portion of the endoscope constituent body protrudes inward in the radial direction and faces the outer circumferential surface of the first frame.

4. The endoscope according to claim 1, wherein the enlarged portion is integrally formed with the distal end portion and with the proximal end portion.

5. The endoscope according to claim 1, wherein the enlarged portion has a flat surface at a distal end side, the flat surface contacting the portion of the endoscope constituent body.

6. The endoscope according to claim 1, further comprising a prism provided proximally relative to the second optical system, the prism configured to separate an image from the first and second optical systems and form each image separately on an image pickup device through first and second optical paths, respectively, the first and second optical paths being different from each other.

7. The endoscope according to claim 1, wherein the endoscope constituent body and the second frame are configured to define a second longitudinal clearance in the longitudinal direction between the endoscope constituent body and the second frame.

8. The endoscope according to claim 7, further comprising an adhesive disposed in the second longitudinal clearance.

9. The endoscope according to claim 1, further comprising an adhesive disposed in the first radial clearance, the second radial clearance and the first longitudinal clearance.

10. An endoscope comprising:
    a first frame configured to hold a first optical system, the first frame comprises:
        a distal end portion;
        an enlarged portion projecting radially from the distal end portion by a height; and
        a proximal end portion;
    a second frame configured to hold a second optical system, the second frame comprises:
        a linkage frame fitted to the proximal end portion; and
        a moving lens frame provided inside of the linkage frame and movable relative to the linkage frame; and
    an endoscope constituent body including a surface that directly contacts a distal surface of the enlarged portion;
    wherein the first frame and the second frame are configured to define a first radial clearance in a radial direction between an outer circumferential surface of the proximal end portion of the first frame and an inner circumferential surface of the linkage frame of the second frame; and
    the first frame and the endoscope constituent body are configured to define a second radial clearance in the radial direction between an outer circumferential surface of the distal end portion of the first frame and the portion of the endoscope constituent body; and
    the height of the enlarged portion is greater than a magnitude of a sum of the first radial clearance and the second radial clearance.

11. The endoscope according to claim 10, wherein the first frame and the second frame are configured to define a first longitudinal clearance in a longitudinal direction between a proximal side of the enlarged portion of the first frame and a distal end side of the linkage frame of the second frame.

12. The endoscope according to claim 11, wherein the endoscope constituent body and the second frame are configured to define a second longitudinal clearance in the longitudinal direction between the endoscope constituent body and an outer surface of the linkage frame of the second frame.

13. An endoscope comprising:
    a first frame configured to hold a first optical system, the first frame comprises:
        a distal end portion;
        an enlarged portion provided proximally relative to the distal end portion, the enlarged portion projecting radially from the distal end portion by a height; and
        a proximal end portion provided proximally relative to the enlarged portion;
    a second frame configured to hold a second optical system, the second frame comprises:
        a linkage frame fitted to the proximal end portion; and
        a moving lens frame provided inside of the linkage frame and movable relative to the linkage frame;

an endoscope constituent body including a surface that directly contacts a distal surface of the enlarged portion;

wherein an inner circumferential surface of the linkage frame is provided offset radially by a first distance from an outer circumferential surface of the proximal end portion;

an inner circumferential surface of the portion of the endoscope constituent body is provided offset radially by a second distance from an outer circumferential surface of the distal end portion; and the height of the enlarged portion is greater than a magnitude of a sum of the first radial distance and the second radial distance.

14. The endoscope according to claim 13, wherein the portion of the endoscope constituent body protrudes inward in a radial direction and faces the outer circumferential surface of the distal end portion.

15. The endoscope according to claim 13, wherein the enlarged portion has a flat surface at a distal side, the flat surface contacting the portion of the endoscope constituent body.

16. The endoscope according to claim 13, further comprising a prism provided proximally relative to the second optical system, the prism configured to separate an image from the first and second optical systems and form each image separately on an image pickup device through first and second optical paths, respectively, the first and second optical paths being different from each other.

17. The endoscope according to claim 13, further comprising an adhesive disposed:

between the inner circumferential surface of the linkage frame and the outer circumferential surface of the proximal end portion, and between the inner circumferential surface of the portion of the endoscope constituent body and the outer circumferential of the distal end portion.

18. The endoscope according to claim 13, wherein the enlarged portion is integrally formed with the distal end portion and with the proximal end portion.

* * * * *